United States Patent
Hecker et al.

(10) Patent No.: US 6,427,694 B1
(45) Date of Patent: Aug. 6, 2002

(54) NASAL BREATHING MASK

(75) Inventors: Karl-Heinz Hecker, Aschau; Rudolf Schinagl, Unterhaching, both of (DE)

(73) Assignee: MPV-TRUMA Gesellschaft fur Medizintechnische Produkte GmbH (DE)

(*) Notice: Subject to any disclaimer, the term of this patent is extended or adjusted under 35 U.S.C. 154(b) by 0 days.

(21) Appl. No.: 09/721,041

(22) Filed: Nov. 22, 2000

(51) Int. Cl.[7] ............................................. A62B 18/02
(52) U.S. Cl. ........................... 128/206.21; 128/201.22; 128/201.23; 128/205.25; 128/206.12; 128/206.24; 128/206.27; 128/206.28; 128/207.13; 128/207.18
(58) Field of Search ................. 128/201.22, 201.23, 128/201.24, 205.25, 206.12, 206.13, 206.18, 206.21, 206.24, 206.27, 206.28, 207.13, 207.18

(56) References Cited

U.S. PATENT DOCUMENTS

| | | | | |
|---|---|---|---|---|
| 1,081,745 A | * | 12/1913 | Johnston et al. | 128/207.13 |
| 5,042,478 A | * | 8/1991 | Kopala et al. | 128/207.18 |
| 5,357,945 A | * | 10/1994 | Messina | 128/200.14 |
| 5,687,715 A | * | 11/1997 | Landis et al. | 128/207.18 |
| 5,746,201 A | * | 5/1998 | Kidd | 128/206.24 |
| 6,112,746 A | * | 9/2000 | Kwok et al. | 128/207.13 |
| 6,119,693 A | | 9/2000 | Kwok et al. | 128/207.11 |
| 6,123,071 A | * | 9/2000 | Berthon-Jones et al. | 128/204.18 |
| 6,192,886 B1 | * | 2/2001 | Rudolph | 128/207.13 |
| 6,237,592 B1 | * | 5/2001 | Surjadi et al. | 128/204.21 |

FOREIGN PATENT DOCUMENTS

WO   WO 99/65554   12/1999

* cited by examiner

Primary Examiner—John G. Weiss
Assistant Examiner—Darwin P. Erezo
(74) Attorney, Agent, or Firm—Marshall Gerstein & Borun

(57) ABSTRACT

The invention relates to a nasal breathing mask having a mask part (1) and a mask-holding part (2), which at the top end is connected to an elongate tube (3) which in turn is connected to a hose connection for a breathing hose and on which a forehead plate (10), connected to a forehead-plate mount (11), is axially adjustable, a region (9) which is more flexible than the rest of the tube (3) being designed and arranged along the path of the tube (3) in such a way that the mask part can be moved toward the user with respect to the forehead-plate mount (11), in order to allow adjustment as a function of the patient's anatomy.

18 Claims, 6 Drawing Sheets

NASAL BREATHING MASK

FIELD OF THE INVENTION

The invention relates to nasal breathing masks.

The invention relates to a nasal breathing mask according to the preamble of Claim 1.

BACKGROUND OF THE INVENTION

Nasal breathing masks are used, inter alia, to supply respiratory air primarily for therapeutic purposes, such as for example for treating disturbed sleep accompanied by apnea.

Conventional breathing masks consist of a partially elastic mask part, which is anatomically shaped in order to be adapted to the patient, and a mask-holding part, to which the straps of the breathing mask are attached in order to press the mask part onto the nose. The respiratory air can be supplied through a breathing tube via a hose connection on the mask-holding part. In this case, the respiratory air is usually taken from a unit which generates superatmospheric pressure.

U.S. Pat. No. 6,119,693 has disclosed a nasal breathing mask having a mask part and a mask-holding part which is connected to at least one strap for positioning the breathing mask on the nose of a user and at the top end is connected to an elongate tube, which in turn is connected to a hose connection for a breathing hose and on which a forehead plate, which is connected to a forehead-plate mount, is axially adjustable. The axial adjustment is in this case effected by means of vertical displacement of the forehead-plate mount, which is designed as a sleeve, on the elongate tube.

Furthermore, in this nasal breathing mask which is known from the prior art, it is possible to compensate for the distance between the patient's forehead and nose in the frontal plane. For this purpose, the breathing mask from the prior art provides for the forehead-plate mount to be designed as a distance-adjustment device. This is achieved by the fact that arms which are rotatably attached to the elongate tube can be releasably latched into attachment openings provided on the rear side of the forehead-plate mount. To make it easy to adjust the breathing mask to different forehead/nose anatomies, it is sufficient for the distance from forehead plate to mask part to be adjusted as a result of the arms being released from a latching position on the forehead-plate mount and secured again in a different latching position, with the angle formed between the arms being adjusted.

However, this solution has the fundamental drawback that designing the distance-adjustment mechanism on the forehead-plate mount in this way leads to a structurally complex forehead plate. The result is considerable production costs if the component, as is customary, is produced using an injection-molding process. Furthermore, the device, which has to be continuously latched and unlatched, has proven unwieldy. Particularly when adapting to the anatomy of the patient, a procedure of this type has proven extremely uncomfortable. A further drawback of this solution is that repeated use of the distance-adjustment device produced in this way leads to wear which may cause the latching lugs formed integrally on the arms to break off, rendering the forehead-plate mount or forehead plate of the nasal breathing mask unusable.

SUMMARY OF THE INVENTION

Working on the basis of these drawbacks which are known from the prior art, the present invention is based on the object of providing a nasal breathing mask which allows simple adjustment to the anatomy of the patient and ensures that the distance-adjustment device functions perfectly without technically complex means having to be used.

According to the invention, this object is achieved by means of a breathing mask according to Claim 1.

Advantageous configurations of the breathing mask according to the invention are given in Claims 2 to 18.

The nasal breathing mask according to the invention having the characterizing features of Claim 1 offers the advantage that the operating comfort when adjusting the breathing mask to the anatomy of the patient is increased while, at the same time, the mask part has a greater freedom of movement with respect to the forehead-plate mount.

In its most simple configuration, the nasal breathing mask according to the invention has a tube between the mask-holding part and the connection for a breathing or intermediate hose. The tube has a region which is designed and arranged in such a way that the mask part can be moved toward the user with respect to the forehead-plate mount, for example as a result of this region being made more flexible than the tube. In other words, the tube may comprise two partial regions with rigid materials properties and a partial region which lies between them and has materials properties which are more flexible than the rigid partial regions. This can be effected, for example as a function of the material used, by a corresponding reduction in diameter and/or reduction in the wall thickness of the tube, as is sufficiently well known.

In its axial extent, the more flexible region is designed in such a way that it offers the possibility of holding the mask part so that it can be moved toward the nose of the user with respect to the forehead-plate mount. The mask part which has been bent onto the user in this way is held by means of corresponding straps which are guided behind the head of the user and are attached to eyelets of the mask part.

In an advantageous configuration of the nasal breathing mask according to the invention, this region can be produced as a result of the tube being designed with at least one airtight ball joint which allows a rotary movement toward the user. Preferably, two ball joints can be arranged over the course of the tube, so that significantly improved adaptation to the patient's anatomy is ensured by means of two degrees of freedom.

According to another advantageous configuration of the invention, the more flexible region comprises a bellows which, as a component of the tube, can be bent in the manner of a drinking straw.

According to yet another advantageous configuration of the nasal breathing mask, the tube is separate from the mask-holding part, the latter bearing a corresponding tube connection piece at the top. The tube and the tube connection piece are connected to one another via a flexurally elastic hose.

Preferably, the flexurally elastic hose itself has a region which is more flexible than the remainder of the hose body, as can be formed, in a manner known per se as a function of the material used for the hose, for example silicone, by a corresponding reduction in diameter and/or reduction in the wall thickness of the hose.

According to the invention, in this case both the tube and the tube connection piece have a sealing bead or a sealing lip, over which the flexurally elastic hose can be pushed so as to form an airtight connection and can be released again in a very simple way.

In order to provide sufficiently great possible compensation for the distance between the forehead or the forehead plate and the nose or the mask part, on the one hand, and to provide the distance-adjustment mechanism defined by the more flexible region with a rigidity which is sufficient for the nasal breathing mask to be used while the patient is sleeping, on the other hand, it is sufficient if the distance which is covered by the flexurally elastic hose between the tube connection piece of the mask-holding part and the tube or the more flexible region of the hose itself is only a few millimeters. By way of example, a distance of even 2 mm is sufficient.

It becomes clear that the embodiments of the invention, compared to the solution which is known from the prior art, provide measures which in design terms are significantly more simple in order to achieve a satisfactory distance-adjustment mechanism. Not only does this considerably reduce production costs, but also, on account of the significantly lower mechanical load, it ensures that the nasal breathing mask has a long service life.

Furthermore, a forehead-plate mount, on which in turn a forehead plate is integrally formed, is connected to the elongate tube which has the more flexible region. In this case, the forehead plate and the forehead-plate mount are preferably produced integrally.

In the prior art, the position of the forehead plate relative to the mask-holding part is adapted to different anatomical conditions by vertical displacement relative to the elongate tube. In the nasal breathing mask which is known from the prior art, for this purpose the forehead-plate mount has a sleeve which can be slid along the tube by means of a corresponding frictional fit. However, when adapting to the corresponding anatomies of the patients, a solution of this type is uncomfortable and, moreover, fails to ensure a secure axial position while the patient is sleeping, which, as a result of the patient moving when asleep, eliminates the distance which has been set and therefore, in extreme cases, may cause the mask part to move and become detached, with associated disturbed and restless sleep.

To avoid these drawbacks, according to another advantageous configuration of the nasal breathing mask according to the invention, the possibility of axial adjustment between the forehead-plate mount and the tube is designed as a latching/clamping connection. Further configurations of the latching/clamping connection according to the invention are given in subclaims 9 to 17.

BRIEF DESCRIPTION OF THE DRAWINGS

Further advantages and advantageous configurations of the invention can be found in the following description in conjunction with the drawing, in which.

DETALIED DESCRIPTION

Figure 1:
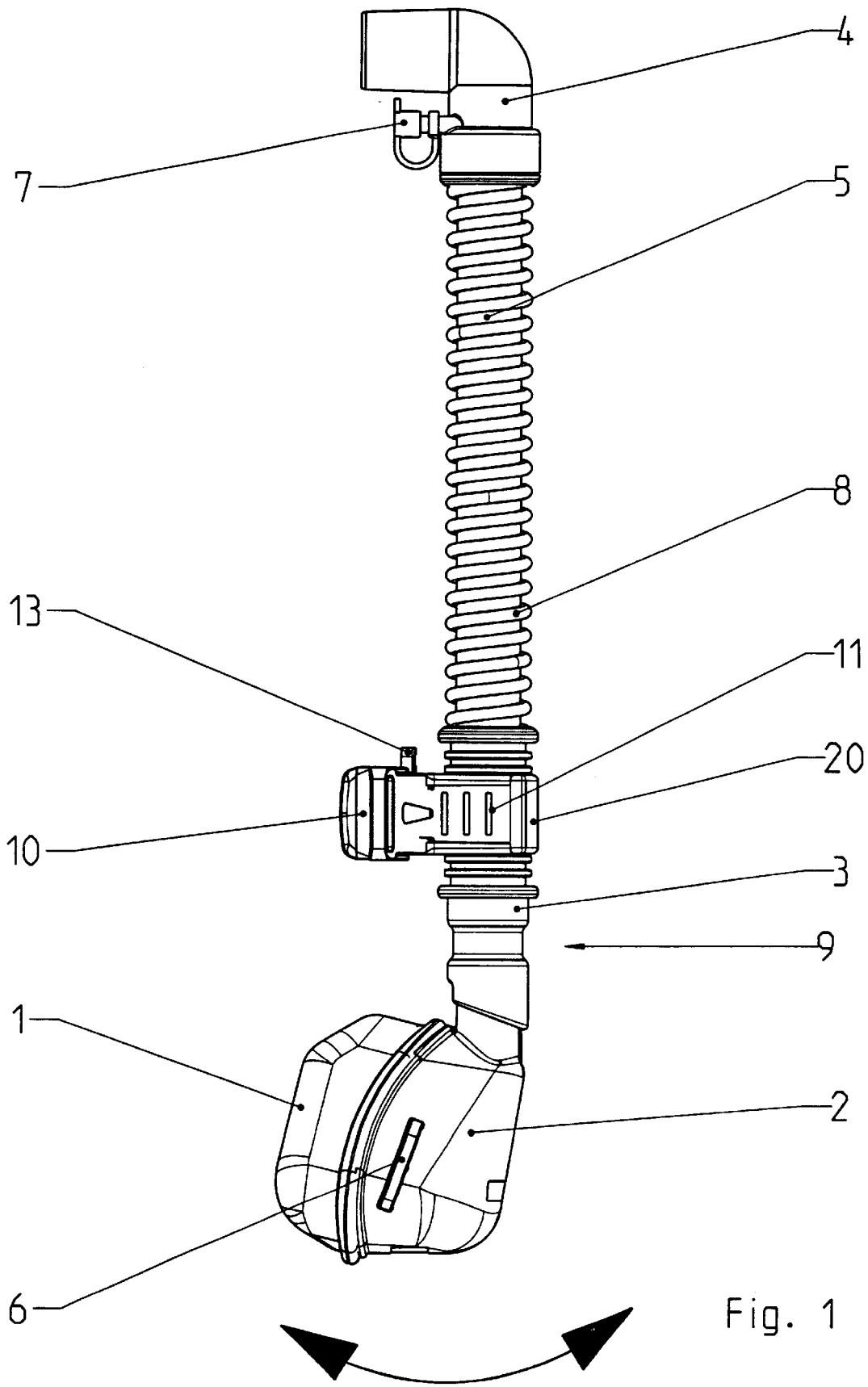
FIG. 1 shows a side view of a first embodiment of a nasal breathing mask according to the present invention.

The first embodiment of a nasal breathing mask, which is shown in FIG. 1, comprises a flexible mask part 1 for adapting the breathing mask to the anatomy of the patient. The flexible and deformable mask part 1 is releasably connected to a mask-holding part 2.

The mask-holding part 2 is vertically adjoined by an elongate tube 3 which is connected to an angle tube 4, as a hose connection for a breathing hose (not shown), via a flexurally elastic intermediate hose 5.

Eyelets 6 for attaching a strap are formed integrally on the mask-holding part 2.

Closeable connection pieces 7 for supplying and/or removing gas to or from the breathing air flowing to the mask part 1 are provided on the angle tube 4, so that, for example, it is possible to carry out measurements in this air or to introduce additives into this air without additional, disruptive lines having to be arranged in the region of the patient's face.

The intermediate hose 5, like the breathing hose (not shown), has a ribbed surface on its outer side and a smooth surface on its inner side, the ribbed surface being formed as a result of a cord 8 running helically around the smooth hose surface and being securely connected thereto. As a result, the hoses are on the one hand, of flexurally elastic design and, on the other hand, are simultaneously secured so that they cannot be pushed off and pinched unintentionally. The smooth surface of the inner side of the intermediate hose 5 ensures that the breathing air flows without turbulence.

The elongate tube 3 arranged between the intermediate hose 5 and the mask-holding part 2 has a region 9 which is designed to be more flexible than the remaining body of the tube 3.

Figure 2:
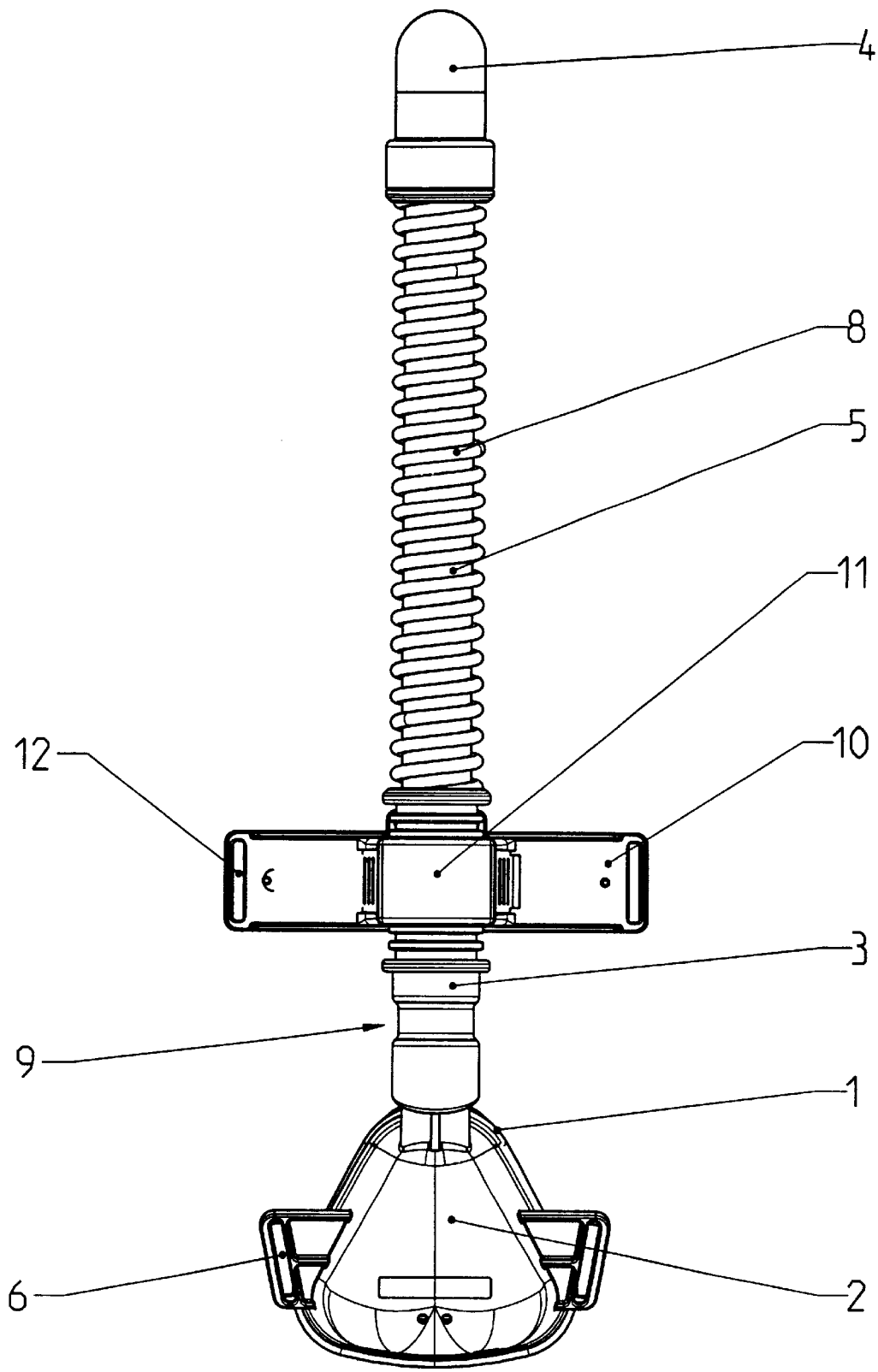
FIG. 2 shows a front view of the breathing mask shown in FIG. 1.

As shown in FIGS. 1 and 2, this more flexible region 9 is produced by means of a reduction in diameter compared to the remaining upper and lower partial region of the tube 3. There is an associated reduction in the wall thickness in this more flexible region 9, with the result that bending is possible, as a function of the material selected for the tube 3, for example silicone, ensuring that the mask-holding part 2 or the mask part 1 can be moved toward the nose of the patient with respect to a forehead plate 10 arranged on the tube 3. In this simple way, it is possible to ensure that the distance between the forehead and the nose in the frontal plane of the patient is compensated for, as indicated by the arrow in FIG. 1.

The forehead plate 10 is connected to the tube 3, at a fixed axial height, via a forehead-plate mount 11. Eyelets 12 and 13 for receiving further straps are formed integrally on the forehead plate 10.

Figure 3:
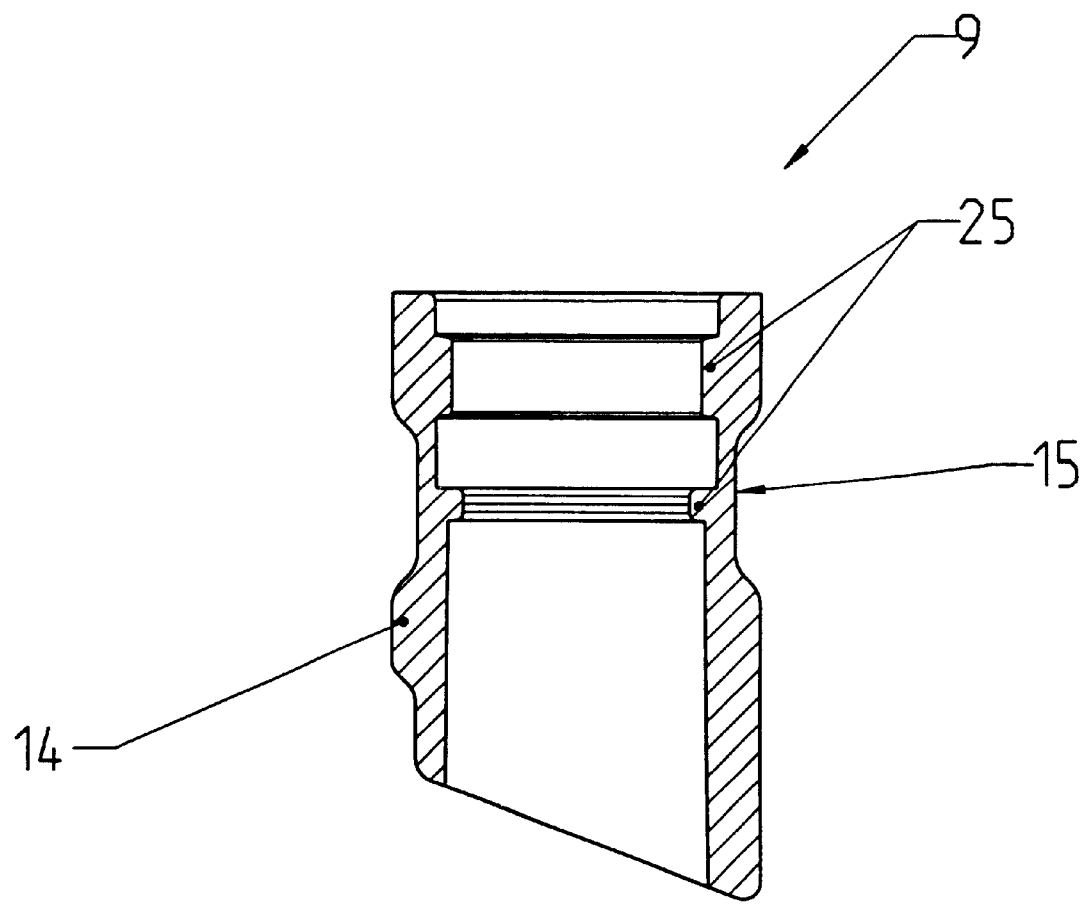
FIG. 3 shows a section through a flexurally elastic hose according to the invention.

FIG. 3 shows a further configuration of the invention. In this configuration, the more flexible region 9 is formed by a flexurally elastic hose 14 which has been pushed onto the tube 3 on one side and onto a tube connection piece formed integrally on the mask-holding part 2 on the other side.

Figure 5:
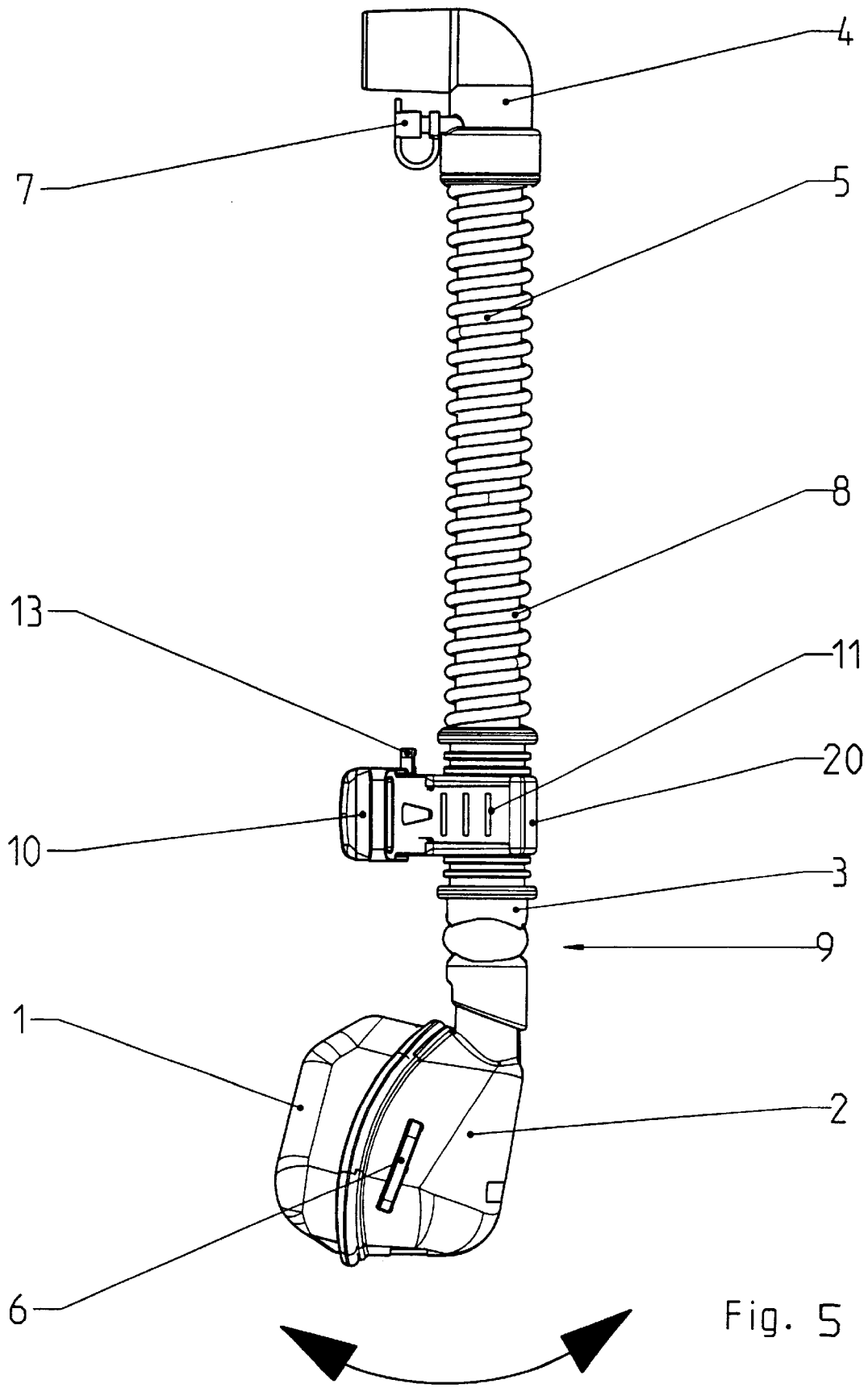
FIG. 5 shows a side view of an alternative embodiment of a nasal breathing mask according to the present invention.
Figure 6:
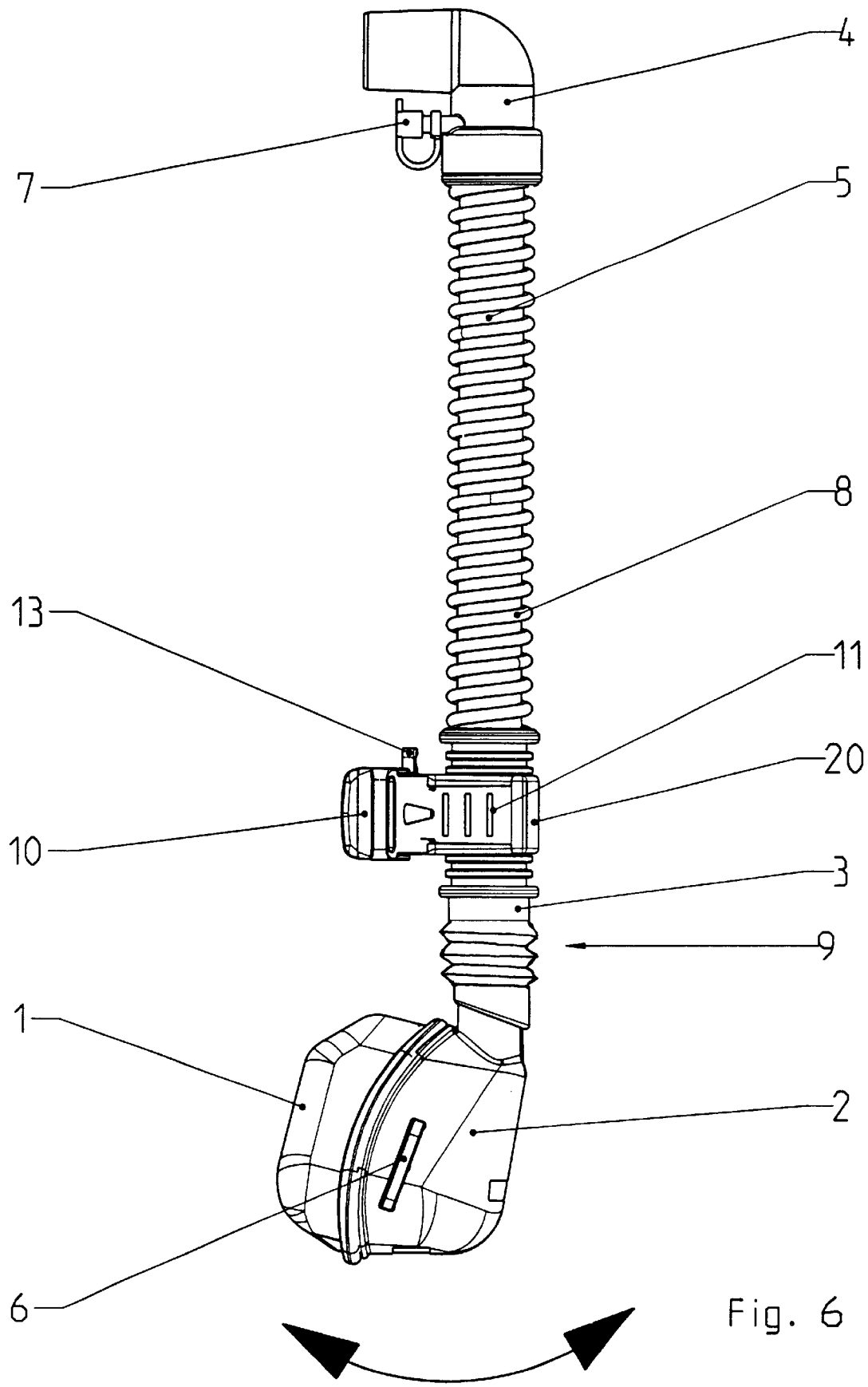
FIG. 6 shows a side view of another alternative embodiment of a nasal breathing mask according to the present invention.

The flexurally elastic hose 14 itself has a region 15 which is more flexible than the remainder of the hose body. As can be seen from the sectional illustration in FIG. 3, the flexibility in the region 15 can be achieved by a simultaneous reduction in the diameter and in the wall thickness of the hose 14. In alternative embodiments, the flexible region 9 may be provided in the form of a ball valve or bellows, as illustrated in FIGS. 5 and 6, respectively.

To ensure an airtight connection at both points, the tube 3 has, in a manner known per se, a sealing bead or a sealing lip 25, over which the flexurally elastic hose 14 is pushed. Depending on the material selected for the flexurally elastic hose 14, it is thus possible, in a simple way, to produce an airtight connection which, on the one hand, can be released at any time and, on the other hand, offers sufficient protection against the nasal breathing mask becoming detached when it is used when the patient is asleep.

In this case, depending on the material of the flexurally elastic hose 14, it is sufficient for the distance covered by this hose between the tube connection piece of the mask-holding part 2 and the tube 3 to be a few millimeters, preferably 2 mm. This type of distance is sufficient to create sufficient adjustability between the forehead-plate mount 11 and the mask part 1.

Figure 4:
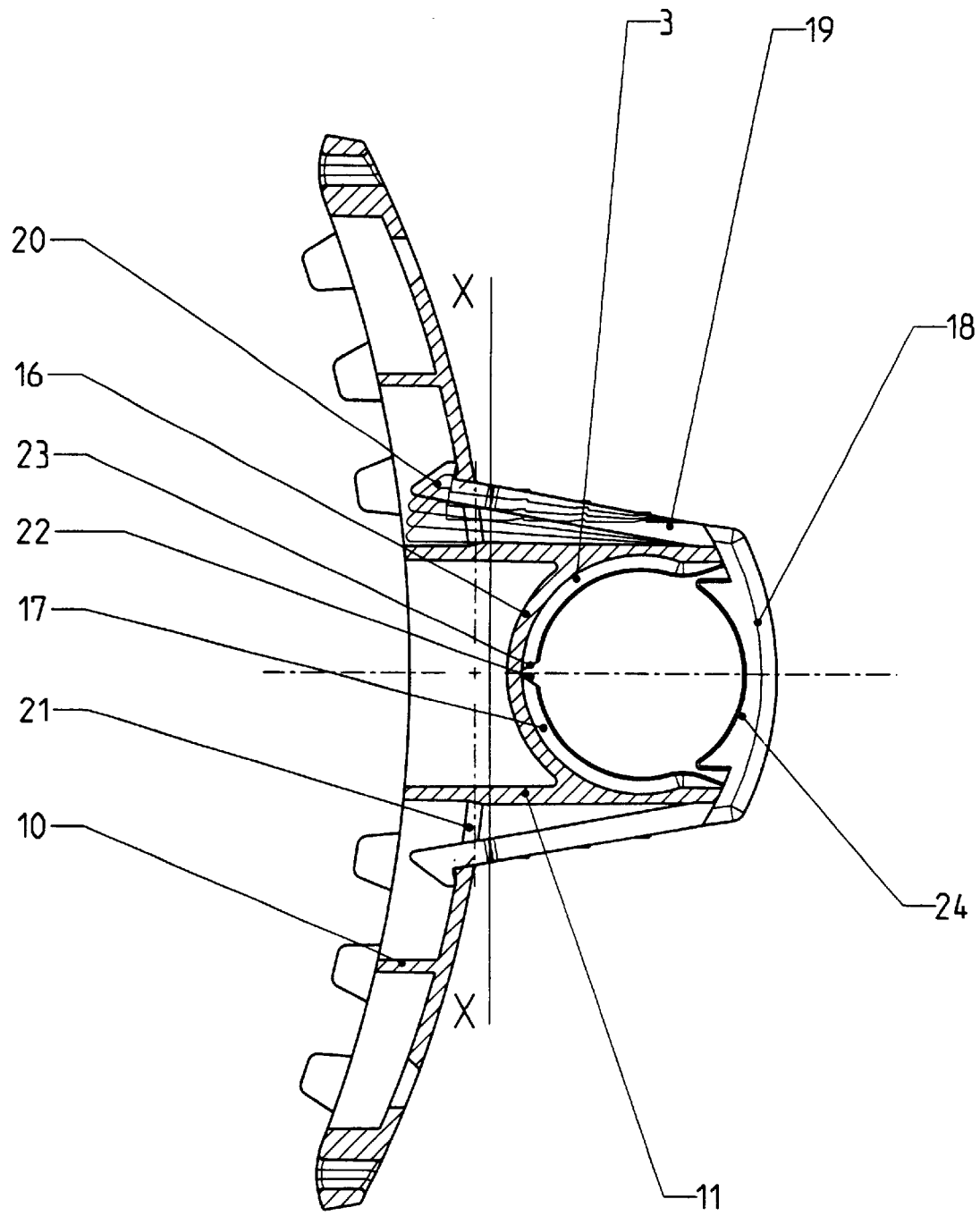
FIG. 4 shows a section through the latching/clamping connection between the forehead-plate mount and the tube.

In an advantageous configuration of the invention, the axial adjustment between the forehead-plate mount 11 and the tube 3 is produced in the manner of a latching/clamping connection, as illustrated in FIG. 4. The forehead-plate mount 11 and the forehead plate 10 are of integral design, the forehead-plate mount 11, in the side remote from the user, extending substantially as a U-shaped collar which is open toward the front. On the inside, the forehead-plate mount 11 has recesses 16 which run parallel to one another in the axial direction and annularly in the circumferential direction. Complementary, annular ribs 17 are inserted in a releasable manner into these equidistantly arranged recesses 16, which ribs are formed integrally and also equidistantly on the circumferential surface of the tube 3.

While the axial height, that is to say the distance between the forehead plate 10 or the forehead of the patient and the mask part 1 or the nose of the patient, is being adapted, the height required can be fixed by means of meshing between the recesses 16 in the forehead-plate mount 11 and the ribs 17 of the tube 3.

To ensure that the tube cannot fall out when it is being positioned, the internal diameter of the collar is slightly less than the external diameter of the tube 3, so that the forehead-plate mount 11 can be latched onto the tube 3 in such a manner that can easily be released again. By gently pulling out the tube 3 and refitting it at a different height, it is possible to carry out a corresponding adjustment according to the individual anatomy of the patient.

If the axial height of the forehead-plate mount 11 has been definitively determined with respect to the tube 3, the arrangement can finally be fixed as a result of the possibility of latching a latching clip 18 onto the forehead-plate mount 11. This latching clip 18 has two limbs 19 which are under a prestress and, at their end, each have a lug 20 which engages in an opening 21 in the forehead plate 10 and, on account of the prestress, can latch in behind this opening, as illustrated in FIG. 4. In this case, the limbs 19 are ideally received in guides which are provided on the outer flanks of the U-shaped collar of the forehead-plate mount 11.

To prevent radial twisting of the tube 3 inside the forehead-plate mount 11 or its U-shaped collar, it is possible for an axially running rib 22 to be formed integrally on the tube 3, which rib can be inserted in a complementary manner in a corresponding axially running groove 23 on the inside of the forehead-plate mount 11.

To provide additional positional fixing, the latching clip 18 has, on its inner side, i.e. on the side facing the user, complementary ribs 24 which can be received in the spaces which are formed by the ribs 17 of the tube 3. It becomes clear that a latching/clamping connection of this type provides a sufficiently secure position of the tube 3 inside the forehead-plate mount 11 while at the same time this arrangement can be released again at any time for anatomically related adjustment measures.

What is claimed is:

1. A nasal breathing mask having:
   a mask part;
   a mask-holding part adapted to receive at least one strap for positioning the mask part on a nose of a user;
   a tube having a first end connected to a top end of the mask-holding part and a second end;
   a breathing hose having a hose connection attached to the tube second end;
   a forehead-plate mount coupled to the tube such that the forehead-plate mount is axially adjustable; and
   a forehead plate connected to the forehead-plate mount;
   wherein the tube includes a flexible region positioned between the mask-holding part and the forehead-plate mount so that the mask part is movable toward the user with respect to the forehead-plate mount.

2. The nasal breathing mask of claim 1, in which the flexible region of the tube includes at least one ball joint or bellows.

3. The nasal breathing mask of claim 1, in which a flexurally elastic hose is provided between the mask-holding part and the tube.

4. The nasal breathing mask of claim 3, in which the flexurally elastic hose includes a region having a greater flexibility than a remainder of the hose.

5. The nasal breathing mask of claim 3, in which the mask-holding part has a tube connection piece with a sealing lip over which the flexurally elastic hose is pushed to form a seal.

6. The nasal breathing mask of claim 5, in which the first end of the tube includes a sealing lip over which the flexurally elastic hose is pushed to form a seal.

7. The nasal breathing mask of claim 5, in which a distance over which the flexurally elastic hose extends between the tube connection piece and the tube is approximately 2 mm.

8. The nasal breathing mask of claim 1, in which the forehead-plate mount is coupled to the tube with a releasable latching clamping connection that allows axial adjustment of the forehead-plate mount along the tube.

9. The nasal breathing mask of claim 8, in which a side of the forehead-plate mount remote from the user includes a substantially U-shaped collar having an open end extending away from the user, an inside of the collar having recesses extending parallel to one another in an axial direction and annularly in a circumferential direction, and in which a circumferential surface of the tube is formed with annular ribs sized for releasable insertion into the recesses.

10. The nasal breathing mask of claim 9, in which the collar has an internal diameter that is slightly smaller than an external diameter of the tube, so that the forehead-plate mount is releasably latchable onto the tube.

11. The nasal breathing mask of claim 9, in which the recesses and ribs are arranged equidistantly in the axial direction.

12. The nasal breathing mask of claim 9, further comprising a latching clip adapted to releasably latch onto a side of the forehead-plate mount remote from the user.

13. The nasal breathing mask of claim 12, in which the latching clip includes two prestressed limbs, an end of each limb having a lug, and in which the forehead plate includes openings sized to receive the lugs such that the prestressed limbs releasably latch the lugs behind the openings.

14. The nasal breathing mask of claim 13, in which a side of the latching clip facing the user includes ribs adapted for insertion into spaces formed between adjacent ribs of the tube.

15. The nasal breathing mask of claim 13, in which an outside of the collar is formed with guides sized to receive the limbs of the latching clip.

16. The nasal breathing mask of claim 8, in which the tube includes an axially extending rib and the forehead-plate mount includes an axially extending groove sized to receive the axially extending tube rib.

17. The nasal breathing mask of claim 1, in which the forehead-plate mount is formed integrally with the forehead plate.

18. The nasal breathing mask of claim 1, in which the mask part and forehead plate are formed of silicone.

* * * * *